(12) United States Patent
Baloa Welzien et al.

(10) Patent No.: US 9,757,532 B2
(45) Date of Patent: Sep. 12, 2017

(54) DETECTION OF PATIENT INTERFACE DISCONNECT FOR CONTROLLING CONTINUOUS POSITIVE AIRWAY PRESSURE THERAPY

(71) Applicant: Breathe Technologies, Inc., Irvine, CA (US)

(72) Inventors: Leonardo Alberto Baloa Welzien, Lake Forest, CA (US); Mark Pielemeier, Irvine, CA (US); Samir S. Ahmad, San Diego, CA (US)

(73) Assignee: Breathe Technologies, Inc., Irvine, CA (US)

( * ) Notice: Subject to any disclaimer, the term of this patent is extended or adjusted under 35 U.S.C. 154(b) by 511 days.

(21) Appl. No.: 14/181,435

(22) Filed: Feb. 14, 2014

(65) Prior Publication Data

US 2015/0231350 A1    Aug. 20, 2015

(51) Int. Cl.
*A61M 16/00* (2006.01)
*A61M 16/06* (2006.01)
*A61M 16/20* (2006.01)

(52) U.S. Cl.
CPC .... *A61M 16/0069* (2014.02); *A61M 16/0051* (2013.01); *A61M 16/06* (2013.01); *A61M 16/208* (2013.01); *A61M 2016/0027* (2013.01); *A61M 2205/3331* (2013.01); *A61M 2205/42* (2013.01); *A61M 2205/50* (2013.01); *A61M 2205/52* (2013.01); *A61M 2230/18* (2013.01); *A61M 2230/40* (2013.01)

(58) Field of Classification Search
CPC .......... A61M 16/0051; A61M 16/0069; A61M 16/00; A61M 16/0066; A61M 2016/0015; A61M 2016/0027; A61M 2230/40
See application file for complete search history.

(56) References Cited

U.S. PATENT DOCUMENTS

| 3,848,591 A | 11/1974 | Smythe et al. |
| 3,870,012 A * | 3/1975 | Metivier ................ A61B 5/113 116/268 |

(Continued)

OTHER PUBLICATIONS

ISR and Written Opinion for PCT/US2015/014876. Issued on Apr. 21, 2015.

*Primary Examiner* — Kathryn E Ditmer
(74) *Attorney, Agent, or Firm* — Stetina Brunda Garred and Brucker; Mark B. Garred (57) ABSTRACT

Methods for detecting a patient disconnecting from a continuous positive airway pressure (CPAP) therapy device are disclosed. A cyclical pressure difference signal is derived based upon measurements from a patient interface pressure sensor and from a source pressure sensor. The pressure difference signal is integrated to generate a resultant integral signal for each respiratory cycle, which is comprised of at least one inspiratory phase and at least one expiratory phase as represented by the corresponding portions of the pressure difference signal. A pressure source of the CPAP therapy device is deactivated in response to a disconnect condition being evaluated from the integral signal. In one embodiment, the disconnect condition is the integral signal exceeding a predefined disconnect threshold. In other, it is a slope value corresponding to a rate of increase of the integral signal exceeding a predefined threshold for a predefined duration.

11 Claims, 5 Drawing Sheets

(56) References Cited

U.S. PATENT DOCUMENTS

| | | | |
|---|---|---|---|
| 4,155,357 A | 5/1979 | Dahl | |
| 5,458,137 A * | 10/1995 | Axe | A61F 5/56 128/204.21 |
| 5,640,149 A | 6/1997 | Campbell | |
| 6,085,747 A | 7/2000 | Axe et al. | |
| 6,173,711 B1 | 1/2001 | Ruton | |
| 6,240,921 B1 * | 6/2001 | Brydon | A61M 16/00 128/204.18 |
| 6,308,706 B1 | 10/2001 | Lammers et al. | |
| 2006/0086357 A1 * | 4/2006 | Soliman | A61M 16/0051 128/204.22 |
| 2006/0137687 A1 | 6/2006 | Colla et al. | |
| 2008/0053441 A1 * | 3/2008 | Gottlib | A61M 16/0051 128/204.23 |
| 2008/0060656 A1 * | 3/2008 | Isaza | A61M 16/0468 128/207.16 |
| 2010/0147303 A1 | 6/2010 | Jafari et al. | |
| 2012/0157794 A1 | 6/2012 | Goodwin et al. | |
| 2013/0228180 A1 | 9/2013 | Ahmad et al. | |
| 2013/0239960 A1 * | 9/2013 | Bertinetti | A61M 16/0066 128/202.22 |
| 2015/0182710 A1 * | 7/2015 | Berry Ann | A61M 16/0066 128/204.21 |

\* cited by examiner

DETECTION OF PATIENT INTERFACE DISCONNECT FOR CONTROLLING CONTINUOUS POSITIVE AIRWAY PRESSURE THERAPY

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates generally to the treatment of respiratory conditions with continuous positive airway pressure (CPAP) devices, and more particularly, to detection of patient interface disconnect for controlling CPAP therapy.

2. Related Art

Sleep apnea is a serious medical condition in which patient breathing during sleep pauses abnormally, or is abnormally low. Apnea is categorized as obstructive, central, and combined obstructive and central, though the obstructive sleep apnea (OSA) is the most common. The patient's upper airway repeatedly narrows or collapses, causing pauses in breathing that may extend in duration up to half a minute. Although some degree of apnea is considered normal, in more severe cases, daytime sleepiness and fatigue may result as a consequence of reduced blood oxygen saturation, as well as constant interruptions to sleep cycles because of patients gasping for air. There have been studies linking sleep apnea to more severe long-term health issues including heart disease and depression, and recently, to cancer as well. With apnea being strongly linked to obesity, and with obesity being projected to increase, the number of patients suffering from sleep apnea is likely to increase concomitantly.

One common treatment for obstructive sleep apnea is continuous positive airway pressure (CPAP) therapy, where a positive pressure is applied to the patient to prevent its collapse as would otherwise occur during an apnea episode. By retaining the patient's airway, normal, uninterrupted breathing during sleep is ensured. In a basic implementation, CPAP therapy applies a constant pressure that is not tied to the patient's normal breathing cycle. The positive airway pressure is desired in the inspiratory phase when the pressure differences between the lungs and the nose contribute to the collapse of the intermediate airway.

Earlier patient breathing assistance devices tended to be uncomfortable to use because of the bulkiness associated with the patient interface, as well as the misapplication of pressure resulting from sub-optimal control methodologies. The application of pressure, no matter how slight, against respiratory efforts of the patient can cause a sense of asphyxiation because of the corresponding increase in work of breathing that can be sufficiently distracting to cause difficulties for the patient to fall asleep. Various improvements have been developed to reduce discomfort to the patient during therapy, particularly at critical points along the respiratory cycle. Thus, a therapeutic device that was previously prescribed only for the more severe cases of sleep apnea in which the benefits of treatment outweighed the significant discomfort is now useful for treating a wider spectrum of sleep apnea conditions. Notwithstanding the increased availability of CPAP devices for home use as a result of these technical improvements, ensuring patient compliance with the prescribed treatment has remained a challenge.

Patient comfort or rather, the lack thereof, was not the sole reason for reduced CPAP treatment compliance. The constant high frequency hissing noise of air flowing back and forth from the CPAP device, the patient interface, and the connecting conduits, was and remains a frequent complaint of not only the patient, but of the patient's partners as well. Deliberate efforts have been undertaken to solve the noise issues with improved blowers and sound insulation features integrated into the patient interface and other gas passage conduits.

To a large extent, conventional CPAP devices are quiet when operating normally, that is, with the patient wearing the interface and is correctly connected to the CPAP device with minimal leakage. However, when any part is disconnected, a substantial amount of noise is generated while the CPAP device continues to operate and the blower continues to generate airflow. Although ideally the patient will experience continuous and uninterrupted sleep, this is oftentimes not the case. The patient may need to disconnect from the CPAP device for any number of reasons such as bathroom breaks, getting a drink of water, and so forth. Typically, such disconnections occur while the patient is not fully awake, and therefore may not have an awareness or mental faculty to turn off the CPAP device. Furthermore, the patient interface may also be disconnected unintentionally during sleep.

Outside of the clinical environment where a shared sleeping arrangement is common, the sleeping partner may be roused awake from the excessive noise. Accordingly, there is a need in the art for detecting patients disconnecting from the CPAP device circuit, and in response to detecting such condition, deactivating the CPAP device so that no further airflow noise is generated.

BRIEF SUMMARY

Various embodiments of the present disclosure are directed to deactivating a CPAP therapy device upon detecting that the patient has disconnected therefrom. This may be achieved by analyzing pressure measurements at the patient interface and at the output of the pressure source. One embodiment relies upon a comparison of the integral of pressure measurement differences over time to a predefined threshold, while another embodiment employs a slope of the integral of pressure measurement differences over time.

In accordance with one embodiment, there is disclosed a method for terminating pressure output from a CPAP therapy device in response to a patient disconnect. The method may include deriving a cyclical pressure difference signal based upon measurements from a patient interface pressure sensor in communication with the patient interface and from a source pressure sensor in communication with an output of a pressure source of the CPAP therapy device. Crests of the pressure difference signal may be being representative of patient inspiratory phases, while troughs of the pressure difference signal may be representative of patient expiratory phases. The method may also include a step of integrating the pressure difference signal to generate a resultant integral signal for each respiratory cycle. A given respiratory cycle may be comprised of at least one inspiratory phase and at least one expiratory phase as represented by the corresponding crest and trough of the pressure difference signal. The method may also include deactivating the pressure source in response to a disconnect condition being evaluated from the integral signal. One variation contemplates the disconnect condition as the integral signal exceeding a predefined disconnect threshold. Alternatively, the disconnect condition may be a slope value corresponding to a rate of increase of the integral signal exceeding a predefined threshold for a predefined duration.

Another embodiment may be directed to a method for detecting a patient disconnecting from a CPAP therapy device. The method may include measuring a patient interface pressure and a source pressure. Thereafter, the method may continue with a step of deriving pressure difference values from the measured patient interface pressure and the measured source pressure. The method may include integrating the pressure difference values to generate integral values thereof. There may be a step of resetting the accumulating integral values at each minimum of the pressure difference values. There may also be a step of deactivating the pressure source in response to an evaluation of the integral values exceeding a predefined disconnect threshold.

Yet another embodiment may be directed to a method for detecting a patient disconnecting from a CPAP therapy device. The method may include measuring a patient interface pressure and a source pressure. There may be a step of deriving pressure difference values from the measured patient interface pressure and the measured source pressure. There may also be the same step of integrating the pressure difference values to generate integral values thereof. The method may also include resetting the accumulating integral values at each minimum of the pressure difference values. Then, there may be a step of generating a slope value corresponding to a rate of increase of the integral values. The method may further include deactivating the pressure source in response to an evaluation of the slope value exceeding a predefined disconnect threshold for a predefined duration.

Certain other embodiments of the present disclosure contemplate a non-transitory program storage medium readable by a data processor of a CPAP therapy device that tangibly embodies one or more programs of instructions executable by the data processor to perform the foregoing methods. The present disclosure will be best understood accompanying by reference to the following detailed description when read in conjunction with the drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

The detailed description set forth below in connection with the appended drawings is intended as a description of certain embodiments of the presently disclosed modalities for detecting a patient being disconnected from a continuous positive airway pressure (CPAP) therapy device. Upon detecting such condition, the device may be deactivated to minimize noise, among other reasons. The description sets forth the various functions in connection with the illustrated embodiments, but it is to be understood, however, that the same or equivalent functions may be accomplished by different embodiments that are also intended to be encompassed within the scope of the present disclosure. As such, the particular disclosures herein are not intended to represent the only forms that may be developed or utilized. It is further understood that the use of relational terms such as first and second and the like are used solely to distinguish one entity from another without necessarily requiring or implying any actual such relationship or order between such entities.

Figure 1:
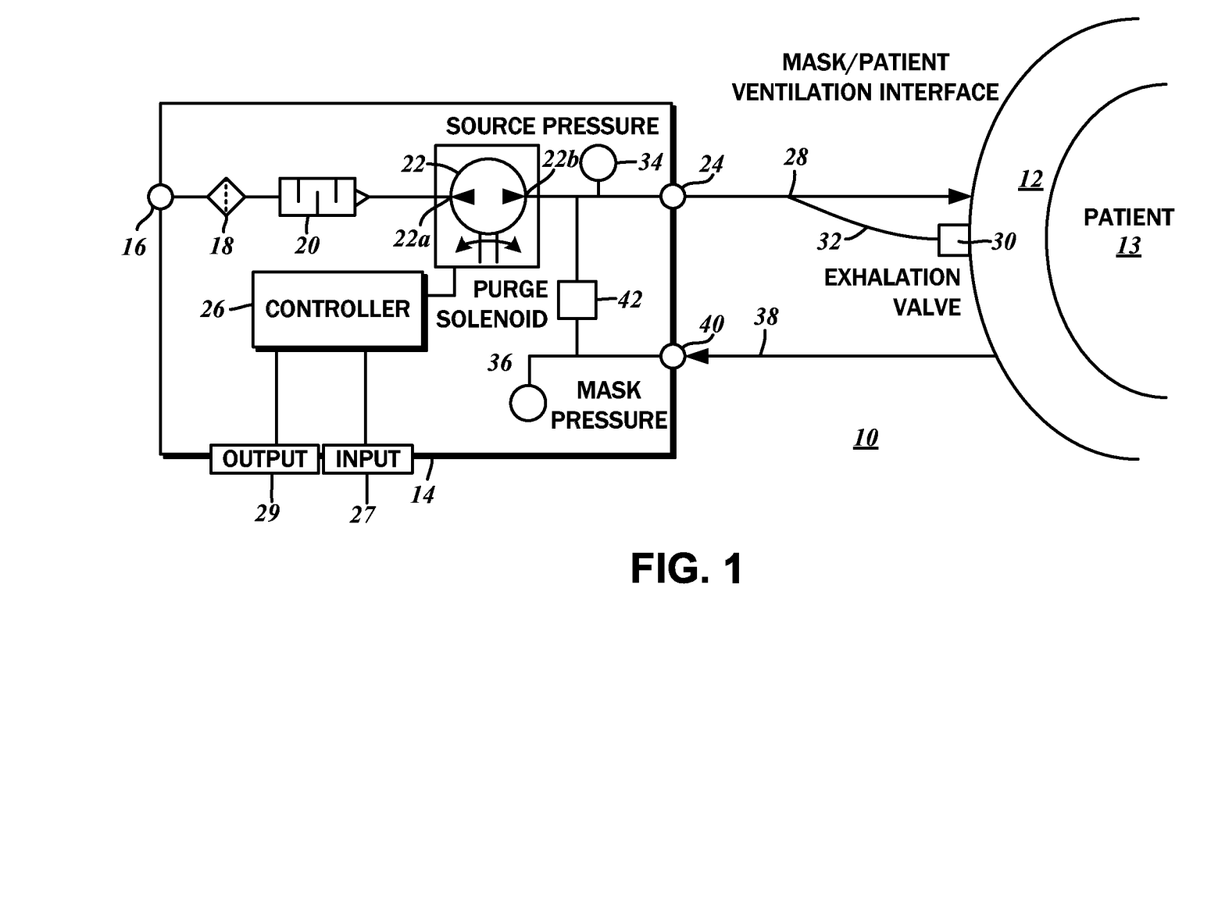
FIG. 1 is a block diagram showing the various components of a CPAP device in accordance with various embodiments of the present disclosure including a typical ventilation unit, a patient ventilation interface, and gas passage conduits.

The block diagram of FIG. 1 illustrates an exemplary airway support device 10 in which various embodiments of the present disclosure may be implemented. There is a mask or patient interface 12, and a ventilation unit 14. The following disclosure will make reference to the patient interface 12 and the mask interchangeably. It is understood to be an apparatus such as a full-face mask or a nasal pillows mask that can be placed in direct gas flow communication with the upper respiratory tract, i.e., the nasal cavity and/or the oral cavity, of a patient 13. It will be appreciated that other apparatuses that so interface the respiratory tract of the patient 13 to the ventilation unit 14 may be substituted without departing from the scope of the present disclosure.

The ventilation unit 14 generates a flow of breathing gas that is delivered to the patient via the patient interface 12. The breathing gas may be ambient air, a combination of ambient air enriched with oxygen, or any other suitable mixture of gas appropriate for treating the patient. Those having ordinary skill in the art will recognize the variety of options for mixing breathing gasses before delivery to the patient. In further detail, the ventilation unit 14 includes a first inlet port 16, through which ambient air is drawn. The first inlet port 16 is in communication with an inlet filter 18 that removes particulates and other contaminants from the breathing gas that is ultimately delivered to the patient. Optionally, in line with the inlet filter 18 is a sound suppressor 20 that reduces the sound of gas flow through the ventilation unit 14.

The force needed for drawing the ambient air through the first inlet port 16, the inlet filter 18, and the sound suppressor 20 is provided by a pressure source 22, which may be a centrifugal fan, blower, or any other suitable device that generates gas flow and pressure suitable for splinting a patient's airway with Continuous Positive Airway Pressure (CPAP) in accordance with the present disclosure. The pressure source 22 has an inlet port 22a coupled to the sound suppressor 20, and an outlet port 22b that is in gas flow communication with an outlet port 24 of the ventilation unit 14.

The pressure source 22 is driven electrically and its actuation is governed by a controller 26, which implements various methods of CPAP treatment such as those disclosed in the co-pending U.S. patent application Ser. No. 13/411, 257 entitled "DUAL PRESSURE SENSOR CONTINUOUS POSITIVE AIRWAY PRESSURE (CPAP) THERAPY," filed Mar. 2, 2012, the disclosure of which is hereby incorporated by reference in its entirety herein. Along these lines, the controller 26 is understood to include a data processing device that receives predetermined instructions to perform various operations, and generate outputs in response. Thus, the contemplated methods can be at least partially implemented therewith. There are input devices 27 that are connected to the controller 26 that accepts inputs from the patient 13, the clinician, or any other operator. The results of executing the instructions may be generated on the output devices 29.

The flow of breathing gas that is output from the pressure source 22 is passed through the outlet port 24 to a gas conduit 28 that is coupled to the aforementioned patient interface 12. The gas conduit 28 is understood to be a plastic tube having a predetermined inner diameter such as 22 mm or smaller, though any other conduit of suitable material and construction may be utilized. The patient interface 12 in accordance with various embodiments of the present disclosure also includes a piloted valve 30 that is selectively actuated depending on the pressure differential between the patient interface 12 and the ventilation unit 14. The piloted valve 30 is connected to a pilot line 32 that branches from the gas conduit 28. A pressure difference is generated between the patient ventilation interface and the exhalation valve, such that it is closed during inspiration and opened during expiration. It will be appreciated that the specifics of the patient interface 12, including the piloted valve 30 thereof, are presented by way of example only and not of limitation. Any other suitable patient interface 12, including those that may be utilized in conjunction with different variations of the ventilation unit 14, may be substituted without departing from the scope of the present disclosure.

In order to ascertain such pressure differentials, the presently contemplated airway support device 10 includes dual pressure sensors, including a source pressure sensor 34 and a patient interface pressure sensor 36. The source pressure sensor 34 is disposed within the ventilation unit 14, and monitors the pressure at the outlet port 22b. The patient interface pressure sensor 36 is also physically disposed within the ventilation unit 14, but is in direct gas flow communication with the patient interface 12 over a pressure sensor line 38 that is connected to a second inlet port 40. When the ventilation unit 14 is operating, gas pressure within the pressure sensor line 38 as well as the gas conduit 28 may be connected to deliver a purge flow to clear line 38. This can be done through a purge solenoid 42 connected to both. The purge can be continuous or intermittent according to the patient's breathing phase or pressure difference between the blower pressure and the mask pressure.

Various embodiments of the present disclosure contemplate an initial step of measuring the pressure at the patient interface 12 and the pressure source 22. These measurements are understood to facilitate control over the pressure levels that are delivered to the patient 13 in coordination with the patient respiratory cycle. Additionally, however, the pressure measurements at the patient interface 12 and the pressure source 22 can be used to determine when the patient 13 becomes disconnected from the airway support device 10.

As referenced herein, patient disconnect may refer to a condition in which the patient 13 is separated from the patient interface 12 by intentional or inadvertent removal of the same, as well conditions in which the patient interface 12 remains coupled to the patient 13 but the gas conduit 28 is disconnected from the patient interface 12 or from the ventilation unit 14, or any combination thereof. Broadly, a patient disconnect is deemed to have occurred when the device-patient circuit is incomplete, for example, when the pressure source 22 is outputting pressure, but the patient 13 does not receive it. Regardless of the particulars, such a condition is understood to waste energy, increase wear, and generate unwanted noise.

Figure 2A:
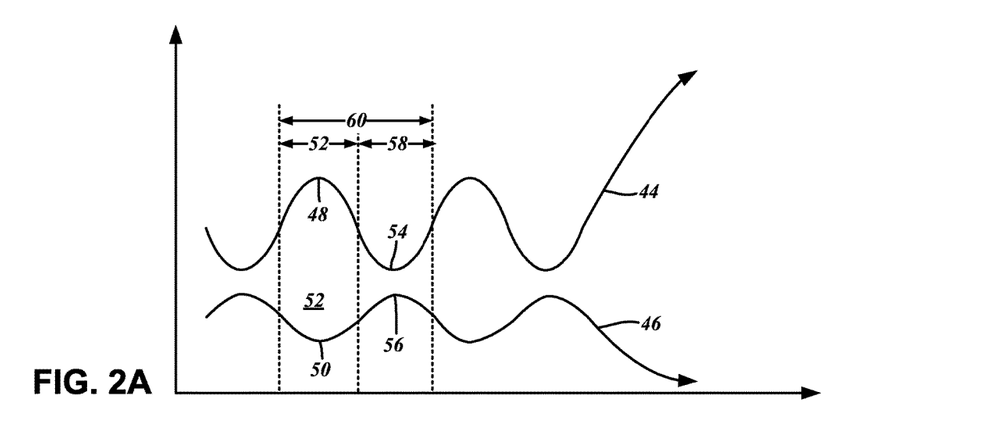
FIG. 2A is a graph plotting measured pressure values at the patient interface and at an output of a pressure source.

The graph of FIG. 2A includes a first plot 44 corresponding to exemplary measurements taken by the source pressure sensor 34 over several patient respiratory cycles, as well as a second plot 46 corresponding to exemplary measurements taken by the patient interface pressure sensor 36. The measurements may be made continuously, so the output of the pressure sensors may be a continuous analog signal. It is also possible to measure and quantify the pressure levels as discrete numeric values with an analog-to-digital converter (ADC).

It is understood that the pressure at the pressure source 22 is inverse to the pressure at the patient interface 12, that is, a peak 48 as shown in the first plot 44 corresponding to the measurements of the source pressure sensor 34 is the same in time as a valley 50 as shown in the second plot 46. This condition is understood to correspond to a patient inspiratory phase 52. Furthermore, a valley 54 as shown in the first plot 44 corresponding to the measurements of the source pressure sensor 34 is the same in time as a peak 56 as shown in the second plot 46. This condition is understood to correspond to a patient expiratory phase 58. The aforementioned patient inspiratory phase 52 and the patient expiratory phase 58 combine to define a patient respiratory cycle 60.

Figure 2B:
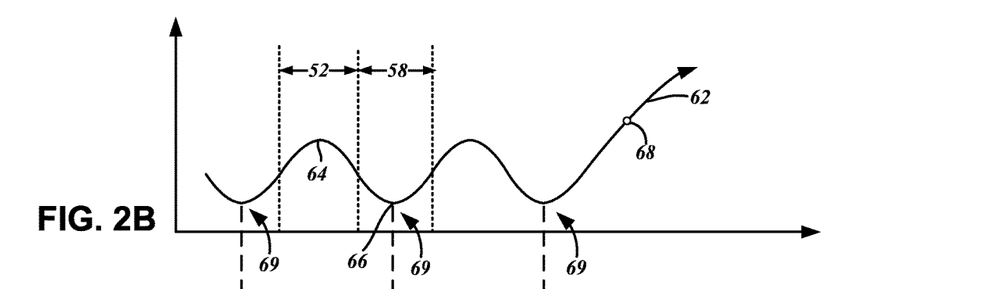
FIG. 2B is a graph plotting the difference between the pressure values at the patient interface and at the output of the pressure source.
Figure 3:
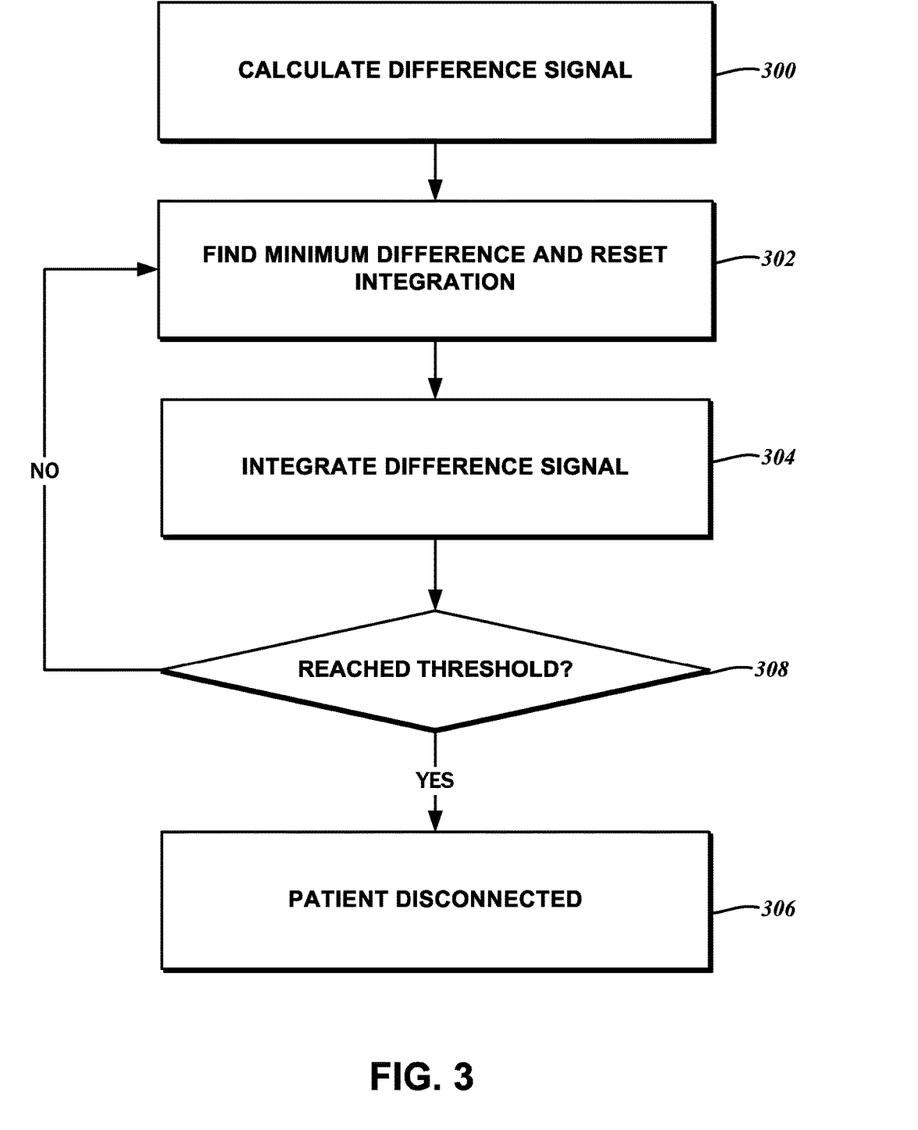
FIG. 3 is a flowchart depicting steps of a first embodiment of a method for detecting a patient disconnecting from the CPAP device.

With reference to the flowchart of FIG. 3, a first embodiment of a method for detecting a patient disconnecting from the airway support device 10, which can also be referred to as a CPAP therapy device, includes a step 300 of calculating a pressure difference signal/discrete values between the measurements from the source pressure sensor 34 and the patient interface pressure sensor 36. This step may also be referred to as deriving a cyclical pressure difference signal. FIG. 2B illustrates an example pressure difference signal, shown as a third plot 62. The greatest pressure difference between the signal from the source pressure sensor 34 and the signal from the patient interface pressure sensor 36 occurs during the aforementioned patient inspiratory phase 52, and corresponds to a crest or peak 64. On the other hand, the least pressure difference between the signal from the source pressure sensor 34 and the signal from the patient interface pressure sensor 36 occurs during the patient expiratory phase 58, and corresponds to a trough or valley 66.

In an exemplary sequence, a patient disconnect occurs at a point 68, after which the pressure difference signal increases to a saturation point. This is understood to correspond to the source pressure (as represented by the first plot 44) increasing to a maximum value, while the ventilation interface pressure (as represented by the second plot 46) decreasing to near zero. Various embodiments of the present disclosure contemplate ways in which the patient disconnect 68 can be identified and distinguished from normal operating conditions in which the pressure measurement signals are cyclical as characterized by alternating crests and troughs.

Figure 2C:
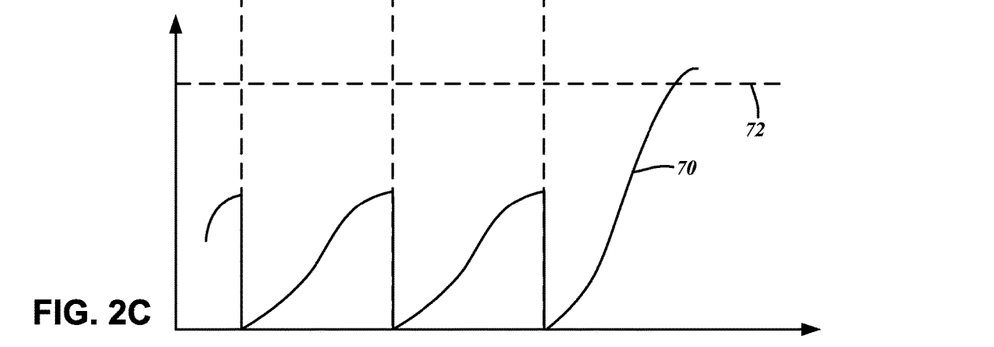
FIG. 2C is a graph plotting an integral of the difference between the pressure values at the patient interface and at the output of the pressure source as shown in FIG. 2C, with a disconnect being detected when the integration reaches a predefined threshold.

The pressure difference signal is then integrated, though prior to this, in a step 302, a minimum 69 of the pressure difference signal is first identified. The integral signal is reset when the minimum of the pressure difference signal is found, and the method then continues with a step 304 of integrating the pressure difference signal. Thus, the pressure difference signal is integrated effectively for each respiratory cycle that includes an inspiratory phase and an expiratory phase. FIG. 2C and a fourth plot 70 depicted therein is understood to represent the integral of the pressure difference signal, including the aforementioned reset points at its minima.

According to multiple embodiments, the patient disconnect 68 is identified and the pressure source 22 is deactivated in response to a disconnect condition being evaluated from the integral signal. This evaluation is understood to occur after the patient disconnect 68 has actually occurred. The deactivation of the pressure source 22 can occur in response to a patient disconnect indication that may be generated, or such indication may be generated independently of the deactivation. Those having ordinary skill in the art will recognize the various ways in which to trigger further action once the patient disconnect is determined.

The evaluation of the disconnect condition can be achieved in various ways. One contemplated variation involves a comparison of the integral signal/integral values to a predefined threshold value 72, as shown in FIG. 2C. This comparison may occur in an decision block 308 in the aforementioned method described in the flowchart of FIG. 3. Once the integral signal exceeds the threshold value 72, then the patient disconnect 68 is deemed to have occurred, and the foregoing deactivation and indication steps are taken. On the other hand, if the integral signal does not yet exceed the threshold, the method returns to the step 302 in which the minimum 69 of the pressure difference signal is identified for resetting the accumulated integral values. Another variation involves a comparison of the rate of change of the integral signal, as will be described in further detail below.

Figure 4A:
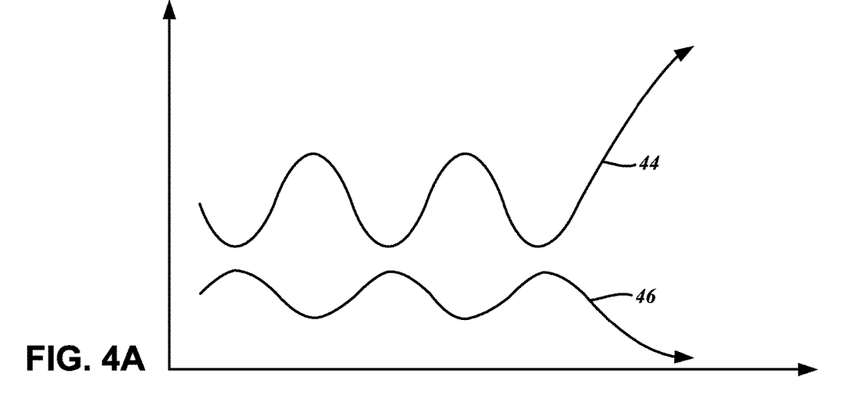
FIG. 4A is a graph plotting measured pressure values at the patient interface and at the output of the pressure source.

With reference to the graph of FIG. 4A, the first plot 44 corresponding to exemplary measurements taken by the source pressure sensor 34 over several patient respiratory cycles is shown, along with the second plot 46 corresponding to exemplary measurements taken by the patient interface pressure sensor 36. The characteristics of the graph of FIG. 4A and what they represent are identical to those shown in the graph of FIG. 2A, and will therefore not be repeated.

Figure 5:
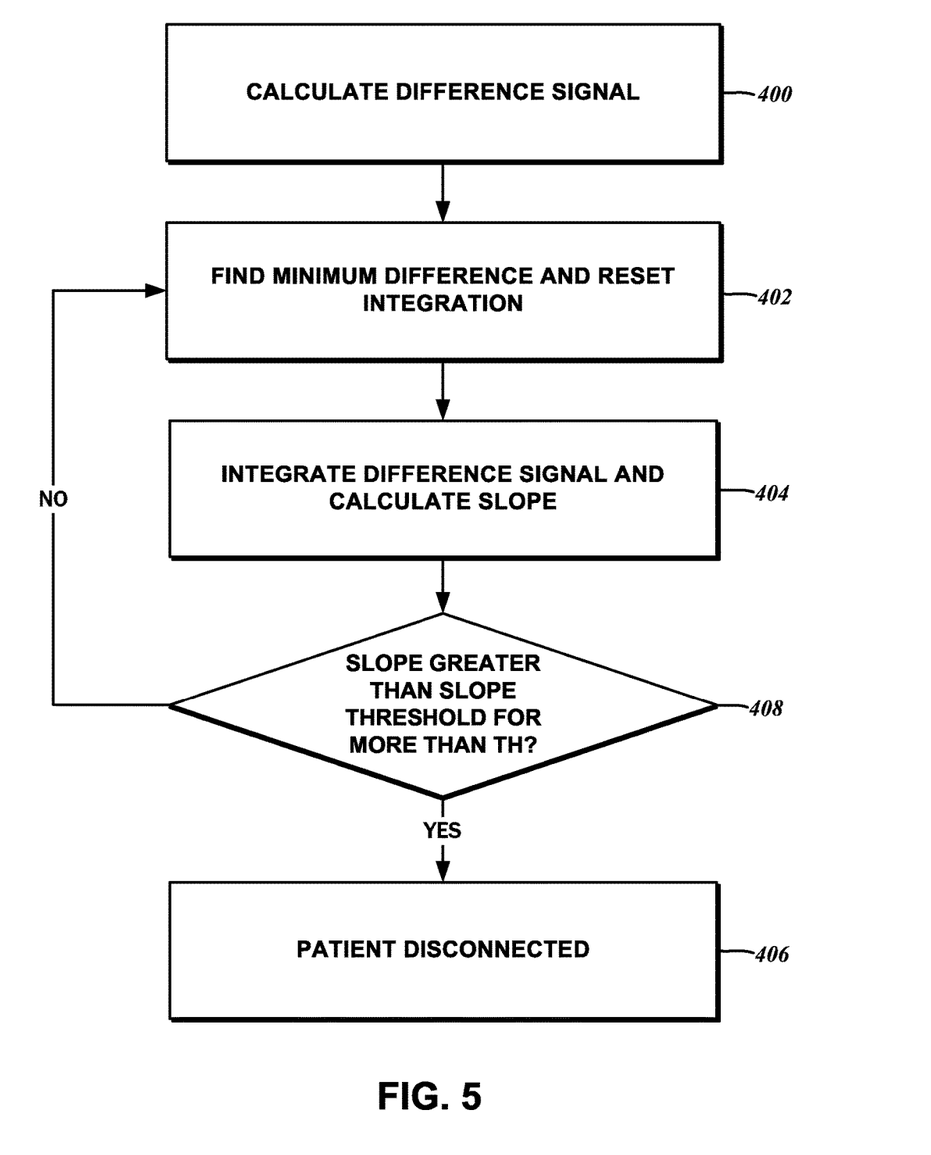
FIG. 5 is a flowchart depicting steps of a second embodiment of the method for detecting the patient disconnecting from the CPAP device.

Referring now to the flowchart of FIG. 5, a second embodiment of a method for detecting a patient disconnecting from the airway support device 10 includes a step 400, similar to the step 300 discussed above with reference to the first embodiment of the method depicted in FIG. 3, of calculating a pressure difference signal/discrete values between the measurements from the source pressure sensor 34 and the patient interface pressure sensor 36.

Figure 4B:
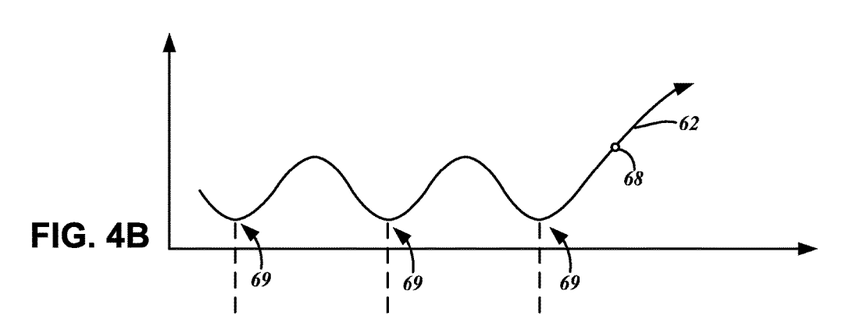
FIG. 4B is a graph plotting the difference between the pressure values at the patient interface and at the output of the pressure source.

FIG. 4B, again similar to the graph of FIG. 2B discussed above, illustrates an example pressure difference signal, shown as the third plot 62. The patient disconnect 68 is also shown to occur at the same time, after which the pressure difference signal increases to a saturation point. Thus, the source pressure (as represented by the first plot 44) increases to a maximum value and the ventilation interface pressure (as represented by the second plot 46) decreases to near zero.

Figure 4C:
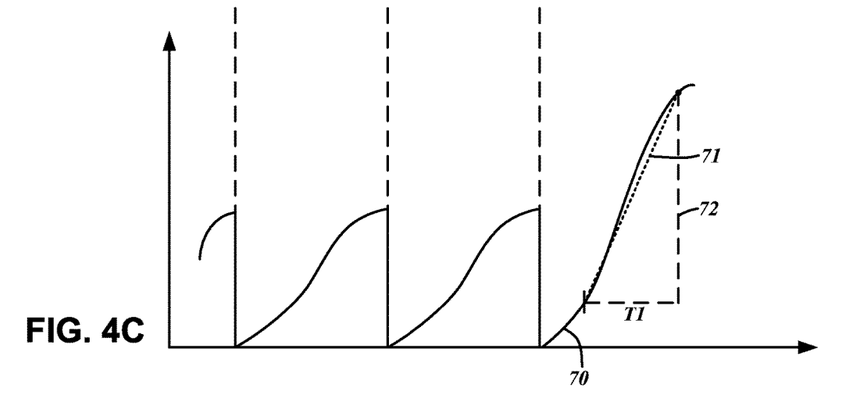
FIG. 4C is a graph plotting an integral of the difference between the pressure values at the patient interface and at the output of the pressure source as shown in FIG. 2C, with a disconnect being detected when a slope of the integral over a predefined duration exceeds a predefined threshold.

The pressure difference signal is then integrated, though prior to this, in a step 402, the minimum 69 of the pressure difference signal is identified. The integral signal is reset when the minimum of the pressure difference signal is found, and the method then continues with a step 404 of integrating the pressure difference signal. As indicated above, the pressure difference signal is integrated for each respiratory. FIG. 4C and the fourth plot 70 depicted therein is understood to represent the integral of the pressure difference signal, including the aforementioned reset points at its minima.

Beyond integrating the pressure different signal, however, the second embodiment of the method contemplates calculating a slope 71 of the integral of the pressure difference signal. This may be determined by a magnitude increase 72 in the integral over a time duration T1 as in a step 408. The patient is deemed to have disconnected when the slope 71 remains above a predefined threshold for more than a predefined duration TH. Once these two conditions are evaluated to exist in the decision block 408, the patient disconnect 68 is identified, and the pressure source 22 is deactivated according to a step 406.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present disclosure with more particularity than is necessary, the description taken with the drawings making apparent to those skilled in the art how the several forms of the present disclosure may be embodied in practice.

What is claimed is:

1. A method for terminating pressure output from a continuous positive airway pressure (CPAP) therapy device in response to a patient disconnect, the method comprising:
    deriving a cyclical pressure difference signal based upon measurements from a patient interface pressure sensor in communication with the patient interface and from a source pressure sensor in communication with an output of a pressure source of the CPAP therapy device, crests of the pressure difference signal being representative of patient inspiratory phases and troughs of the pressure difference signal being representative of patient expiratory phases;
    integrating the pressure difference signal to generate a resultant integral signal;
    generating a slope value corresponding to a rate of increase of the integral signal; and
    deactivating the pressure source in response to a disconnect condition being evaluated from the integral signal;
    wherein the disconnect condition comprises the slope value exceeding a predefined threshold for a predefined duration.

2. The method of claim 1, wherein the patient disconnect occurs prior to the disconnect condition being evaluated.

3. The method of claim 1, further comprising:
    resetting the integral signal at a minimum of the pressure difference signal for a given respiratory cycle.

4. An article of manufacture comprising a non-transitory program storage medium readable by a data processor of a CPAP therapy device, the medium tangibly embodying one or more programs of instructions executable by the data processor to perform a method for terminating pressure output from a CPAP therapy device in response to a patient disconnect, the method comprising:

deriving a cyclical pressure difference signal based upon measurements from a patient interface pressure sensor in communication with the patient interface and from a source pressure sensor in communication with an output of a pressure source of the CPAP therapy device, crests of the pressure difference signal being representative of patient inspiratory phases and troughs of the pressure difference signal being representative of patient expiratory phases;

integrating the pressure difference signal to generate a resultant integral signal;

generating a slope value corresponding to a rate of increase of the integral signal; and deactivating the pressure source in response to a disconnect condition being evaluated from the integral signal;

wherein the disconnect condition comprises the slope value exceeding a predefined threshold for a predefined duration.

5. The article of manufacture of claim 4, wherein the patient disconnect occurs prior to the disconnect condition being evaluated.

6. The article of manufacture of claim 4, the method further including:

resetting the integral signal at a minimum of the pressure difference signal for a given respiratory cycle.

7. A method for detecting a patient disconnecting from a CPAP therapy device, the method comprising:

measuring a patient interface pressure and a source pressure;

deriving pressure difference values from the measured patient interface pressure and the measured source pressure;

integrating the pressure difference values to generate integral values thereof;

resetting the accumulating integral values at each minimum of the pressure difference values;

generating a slope value corresponding to a rate of increase of the integral values;

deactivating the pressure source in response to an evaluation of the slope value exceeding a predefined disconnect threshold for a predefined duration.

8. The method of claim 7, wherein the minima of the pressure difference values correspond to patient expiratory phases and maxima of the pressure difference values correspond to patient inspiratory phases.

9. The method of claim 7, wherein the patient disconnects from the CPAP therapy device prior to the evaluation of the slope value exceeding the predefined disconnect threshold for the predefined duration.

10. The method of claim 7, wherein:

the patient interface pressure is measured by a first sensor in communication with the patient interface; and the source pressure is measured by a second sensor in communication with an output of a pressure source of the CPAP therapy device.

11. The method of claim 7, further comprising:

generating a patient disconnect indication in response to the evaluation of the slope value exceeding the predefined disconnect threshold for the predefined duration.

* * * * *